United States Patent [19]

Hickham

[11] 4,353,691
[45] Oct. 12, 1982

[54] ORTHODONTIC HEADGEAR TRACTION APPLIANCE SYSTEM

[76] Inventor: John H. Hickham, #5 Chateau Palmer Dr., Kenner, La. 70062

[21] Appl. No.: 239,003

[22] Filed: Feb. 27, 1981

[51] Int. Cl.³ .............................................. A61C 7/00
[52] U.S. Cl. ......................................................... 433/5
[58] Field of Search ............................................. 433/5

[56] References Cited
U.S. PATENT DOCUMENTS 4,121,341 10/1978 DeWoskin .............................. 433/5
4,226,589 10/1980 Klein ...................................... 433/5

Primary Examiner—Robert Peshock
Attorney, Agent, or Firm—C. Emmett Pugh & Associates

[57] ABSTRACT

An orthodontic traction appliance system including headgear with straps for the wearer, a face plate on either side connected to the headgear, and a resiliently biased "J"-hook tube assembly on each face plate. The "J"-hook tube assembly comprises a "J"-hook member having a shaft extending through a tube and being resiliently and elastically held into the tube by a rubber band extending between lateral arms on the shaft and a reverse, face plate connecting hook on the underside of the tube. The face plate includes a variable length portion comprising a base portion having series of parallel, lateral, female slots and a head strap connector portion riding on the base portion and having a male, inverted-"L" shaped protrusion for mating with a selected one of the female slots to vary the relative distance between the tube of the "J"-hook assembly and the straps of the headgear.

8 Claims, 5 Drawing Figures

ORTHODONTIC HEADGEAR TRACTION APPLIANCE SYSTEM

BACKGROUND OF THE INVENTION

1. Field of the Invention

The present invention relates to orthodontic retraction appliances, and more particularly to orthodontic headgear having "J" hooks for use in conjunction with so-called braces on teeth in which at least the relative positioning of the headgear and the "J" hooks is adjustable.

2. Prior Art

In orthodontics the use of braces on teeth to reposition and guide them for proper growth is well known. As an accessory to braces in certain situations, it is also desirable to apply an exterior, backward or upwad pulling pressure to the braces by means of spring biased "J" hooks in which the ends of the hooks are attached to the braces and the shanks or shafts of the hooks are attached by resilient biasing means to the headgear or a cap worn by the user. Examples of prior art patents are the U.S. Pat. Nos. to Dewoskin, 2,968,097 issued Jan. 17, 1961, and to Interlandi, 3,203,099 issued Aug. 31, 1965.

However, as a general proposition, these prior art systems were generally not adjustable or as readily or as easily adjustable as desired, and each user usually required a completely customized system, greatly adding to the inconvenience and expense of such systems.

One prior art attempt at making the "J"-hook attachment system adjustable has been the "SNAP-WAY" design of Northwest Orthodontics of Seattle, Wash., in which the "J"-hook assembly included two separate components, an adjustable length latch tab and a calibrated coil spring unit. The latch tab had a series of three, inclined-plane latches while the spring unit had an inverted "U," latch tab guide and an adjacent inverted "U" shape bridge into which the tab would be inserted, until the selected one of the inclined latches had passed through and was held by it. However, such a design has provided relatively little adjustability requiring several different models (for example small, medium, large and extra large for different size patients, is too limited in its application and is relatively more complex and expensive in its manufacture.

It is a basic object of the present invention to provide relatively simple, reliable and easily manufactured, adjustable orthodontic brace biasing systems which are relatively wide ranging in their adjustability and application, allowing for the same orthodontic headgear system to be used for different size patients and for applications requiring different amounts of pull and different directions of pull.

SUMMARY DISCUSSION OF INVENTION

The present invention provides an improved traction system to be used with various types of headgear in configuration with orthodontic retraction appliances. The traction system of the present invention is very simple in design, including basically a rod which slides through a tube. The rod at one end preferably has a shape at least similar to the letter "J," which from hereon will simply be referred to as a "J" hook. The traction system of the present invention can be attached in such a manner so as to allow variability in position in order to better meet the needs of a specific application. An exemplary embodiment will be described in detail below.

The retraction system of the present invention is affixed to the teeth by attaching the "J" hook to the braces on the teeth. The curled end of the "J" hook provides a means for this attachment. From this attachment the "J" hook leaves the mouth, makes a 180° turn, runs some distance, and then passes through the tube which is attached to the headgear.

The traction force on the "J" hook is obtained with the use of for example rubber bands or other elastic or resilient members. The quantity of force depends on the thickness and stretch of the rubber band used. The rubber band is attached at the tube unit at one end, and to the "J" hook at the other end. A place for attaching the rubber band to the "J" hook is provided by means of a cleat having lateral arms or a reverse hook or other lateral protrusion welded or soldered or otherwise connected to the "J" hook at a distance which provides adequate stretch for the rubber band.

In the invention the skull cap portion of the headgear of the present invention provides for a fully adjustable, variable length, "one size fits all" headgear, particularly useful in the high pull type of appliance system. The skull cap preferably comprises two, fixed length, supporting straps that run over the crown of the patient's head. These straps are fastened to two connector sleeves which are located in the temporal region of each side of the patient's head. The connectors also receive one end of a flat band piece of rigid or semi-rigid material which from here on will be referred to as the face plate.

The face plate is able to slide through the connector sleeve. The ability to slide through the connector furnishes the unique adjustable characteristics of the headgear. There is a male projection on the connector and a series of female slots in the face plate. When the desired position or length of the face plate is obtained, its position is fixed by snapping the connector male projection into the corresponding slot in the face plate.

Near the other end of the face plate is the "J" hook traction device summarily discussed above.

BRIEF DESCRIPTION OF THE DRAWINGS

For a further understanding of the nature and objects of the present invention, reference should be made to the following detailed description taken in conjunction with the accompanying drawings in which like part are given like reference numerals and wherein.

1, showing the details of the lateral arm anchoring and stoping cleat on the shaft of "J"-hook member.

DETAILED DESCRIPTION OF PREFERRED EMBODIMENT

Figure 1:
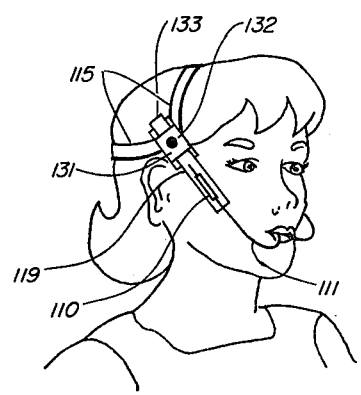
FIG. 1 is a front, perspective view of the preferred embodiment of the orthodontic traction system of the present invention mounted on a high pull type headgear having a, variable length type of face plate.

In the preferred embodiment of FIG. 1 the traction device of the present invention is made up of a rod or "J" hook member 111 which reciprocally slides through a tube 110. The "J" hook member is made of for example a hard temper, stainless steel or comparable material. To the "J" hook member is welded or soldered or otherwise fixedly connected a cleat or hook 112 which is used to accommodate and anchor one end of a closed loop rubber band 113. The shaft of the "J" hook member is straight from its proximal end to the cleat so that it will slide freely in the tube. The distal end of the "J" hook member is curved to accommodate the contours of the patient's face from the cleat to the arch wire hook 116. The arch wire hook 116 is made from the reduced end portion of the "J" hook member which is formed in a hook or eyelet configuration for purposes of attaching the traction unit to the braces on the teeth. The traction device tube can be constructed of any rigid or semi-rigid material, ferrous or non-ferrous.

An exemplary way of attaching the traction tube 110 ultimately to the head straps of the headgear and allowing adjustable positioning between them will be described with reference to FIGS. 1 and 1A, etc.

Figure 5:
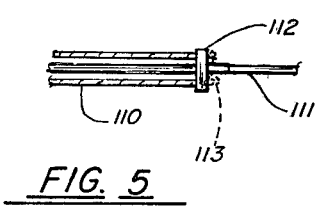
FIG. 5 is a top, partial, cross-sectional view of a portion of the "J"-hook tube element of the system of FIG.

It should be understood that the traction device forms a separate "J" hook tube assembly with all of its sub-elements 110-113 being held together by means of the rubber band 113 extending from and around the lateral arms 112a, 112b (note FIG. 5) of the cleat 112 to and around the base supporting the tube 110 with the rubber band under tension. As best shown in FIG. 5, the shaft of the "J" hook member 111 is drawn into the tube 110 until the arms 112a, 112b serve as stops against the edges of the entry into the tube 110, the arms 112a, 112b extending out on opposite sides of the shaft to a lateral separation distance greater than the inner diameter of the tube 110.

As seen in FIG. 5, the cleat 112 is preferably "T" shaped with the base or shank of the "T" extending along the length of the shaft for fixedly connecting the cleat 112 to the shaft with the base or shank extending away from the tube and toward the distal end of the "J" hook member 111.

It is noted that, for simplicity in illustration purposes, the rubber band 113 is shown in a relaxed position. However, in fact, they are always in stretch under tension from the innermost position (FIG. 5) of the "J" hook member 111 to its outermost position in use on the patient (FIG. 1).

Figure 1A:
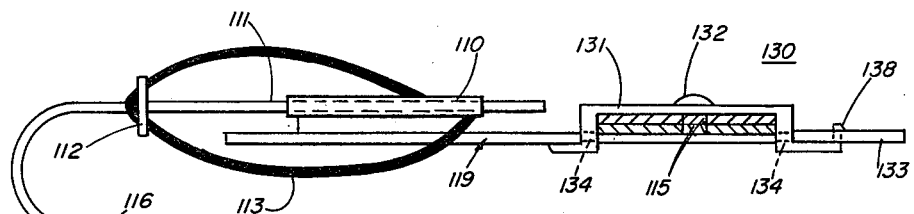
FIG. 1A is an enlarged, side view of the variable length face plate of the high pull headgear of FIG. 1.

In the high pull embodiment of FIGS. 1 and 1A, the traction tube can be (but not necessarily is) fixedly attached to the face plate 119, and the variable positioning of the tube 110 with respect to the head straps 115 is achieved by the face plate 119 having a variable length portion 130. A slidable connector sleeve 131 is fixedly connected by means of for example a brad 132 to the two straps 115 which run over and behind the crown of the head of the patient or wearer to the face plate on the other side of the head of the user. The face plate 119, which is a long flat piece of material, has a base portion 133 which slides though the connector sleeve 131 through lateral end slots 134. The traction device comprising the tube 110 and the "J" hook member 111 is attached at the opposite end of the face plate 119. The hook 111 is in the form of the letter "J" with distal end hook 116 and is connected to the brace on the teeth of the patient.

In FIG. 1 the traction force to the braces is produced by the rubber band 113 to the face plate 119 behind the tube 110 and to the cleat 112 which is affixed to the "J" hook 111.

Figure 3:
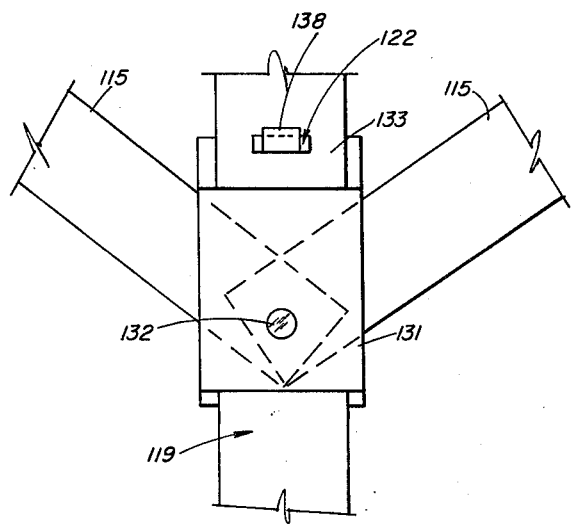
FIG. 3 is a top view of the connector sleeve portion of the headgear of FIG. 1 with straps fastened and the face plate locked in position.
Figure 2:
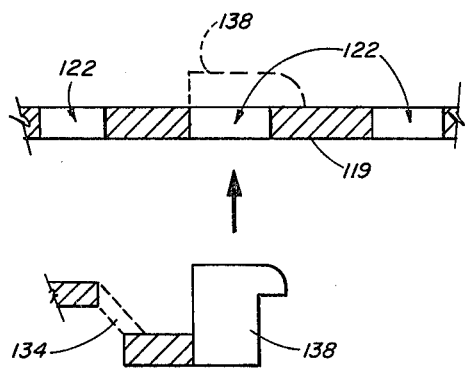
FIG. 2 is an enlarged, partial, cross-section, exploded view showing in detail the male-female locking mechanism for securing the connector sleeve to the base portion of the face plate of the variable length embodiment of FIGS. 1 & 1A.
Figure 4:
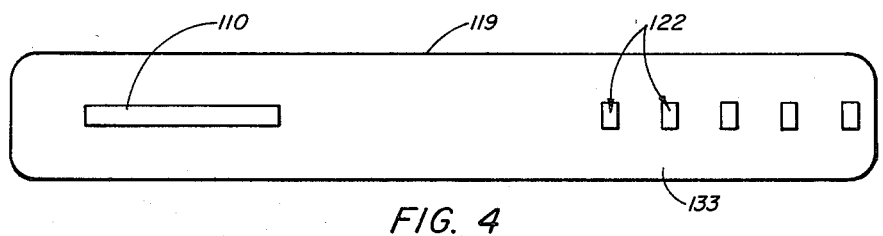
FIG. 4 is a top view of the base portion element of the face plate showing the traction tube and female slots of the embodiment of FIG. 1.

In FIG. 3 the base portion 132 of the face plate 119 is shown locked into place with the connector sleeve 131 by means of the male projection 138 on the connector which is snapped through the selected female slot 122 built into the base portion of the face plate. As can best be seen in the exploded view of FIG. 2, the male member 138 is in the shape of an inverted "L" with the base or shank of the "L" orthogonally extending up from the edge of the sleeve 131 adjacent the end slot 134 with the foot of the "L" snapping over the upper side of the face plate 119 (note phantom line locking position.)

The position of the traction device portion 110-113 of the face plate 119 can be changed with respect to the head straps 115 to accomodate the size of the patient's head or to adjust the force delivered to the braces by the rubber band 113 by pushing the male connector projection 138 back through the face plate slot 122, sliding the base portion 132 of the face plate 119 through the connector 131 to a new position, and then pushing the connector projection back through the then corresponding slot 122. For even greater variability, a variable position face plate with a series of longitudinally spaced openings could be incorporated with the adjustable length portion 130 of the face plate 119 and a removable "J" hook tube assembly with means to attach it to a selected one of the openings in the modified face plate used in place of the fixed tube 110.

Because of the many varying embodiments that may be made within the scope of the inventive concept herein taught, and because many modifications may be made in the embodiment herein detailed in accordance with the disclosure requirements of the law, it is to be understood that the details herein are to be interpreted as illustrative and not in a limiting sense.

What is claimed is:

1. An orthodontic traction appliance system, including headgear having at least two head straps extendable onto both sides of the head of the wearer for wearing by the user, further comprising:
    (a) a first "J"-hook tube assembly having a "J"-hook member resiliently and elastically carried within a tube, and a first face plate positionable along side the side of the face of the wearer to which said first "J"-hook tube assembly is connected and which is attached to said headgear;
    (b) a second "J"-hook assembly having a "J"-hook member resiliently and elastically carried within a tube, and a second face plate positionable along side the opposite side of the face of the wearer to which said second "J"-hook tube assembly is connected and to which is attached to said headgear; each of said face plates, including a variable length portion, each of said variable length portions comprising:
        a flat, longitudinally extended base portion, to which the tube of one of the "J"-hook assemblies is fixed, said base, having a series of like female openings through it and spaced along its length;
        a slideable connector portion, to which the head straps of the headgear are connected, said connector portion riding on said base portion with a top portion over the area of said base portion in which said series of like female openings are located, and said connector portion having spaced lateral slots at both ends through which said base portion extends and said connector portion having a male protrusion extending up from an area adjacent one of said slots for insertion into a selected one of said female openings of said base portion, the availability of said series of like female openings allowing for adjustability of the relative location of the tube of its respective "J"-hook assembly with respect to the straps of the headgear.

2. The orthodontic system of claim 1, wherein said series of like female openings comprise a series of parallel, laterally extending slots.

3. The orthodontic system of claim 1, wherein said male protrusion comprises an orthogonal, inverted-"L" shaped member.

4. The orthodontic system of claim 1, wherein said connector portion has opposed, side openings through which the head straps are extended for fixed connection to said top portion of said connector portion.

5. The orthodonic system of claim 1, wherein each "J"-hook member comprises at its far end a "J" shaped hook attached to an extended shaft reciprocally extending through its respective tube; and lateral protrusions on said extended shaft extending laterally out from it on the portion of said shaft which extends past its respective tube toward said "J" hook; and elastic band means under tension extending from and around said protusions to and around the base of said "U" shaped reverse hook means for resiliently holding and biasing its respective "J"-hook member into its respective tube and hence toward its respective face plate.

6. The orthodontic system of claim 5, wherein said "J"-hook member and said tube are made of stainless steel, and said elastic band means is a closed loop rubber band.

7. The orthodontic system of claim 5, wherein said protrusions form two arms extending out on opposite sides to a lateral distance greater than the inner diameter of said tube, said protrusions serving both as an anchor for one end of said elastic band means and as a stop preventing said elastic band means from pulling said shaft into said tube past the portion of the shaft from which said arms extend.

8. The orthodontic system of claim 7, wherein said protrusions comprise a "T" shaped member, with the base of the "T" extending longitudinally along said shaft in fixed connection therewith with the base of the "T" extending away from said tube.

* * * * *